(12) United States Patent
Langermann et al.

(10) Patent No.: US 6,368,599 B1
(45) Date of Patent: Apr. 9, 2002

(54) CAULOBACTER LPS IMMUNOADJUVANTS

(75) Inventors: Solomon Langermann, Baltimore; Scott Koenig, Rockville, both of MD (US); John Smit, Richmond (CA); Nilofer Qureshi, Madison, WI (US)

(73) Assignee: Univ. of British Columbia, Vancouver (CA)

(*) Notice: Subject to any disclaimer, the term of this patent is extended or adjusted under 35 U.S.C. 154(b) by 0 days.

(21) Appl. No.: 09/510,313

(22) Filed: Feb. 22, 2000

Related U.S. Application Data

(60) Provisional application No. 60/121,120, filed on Feb. 22, 1999.

(51) Int. Cl.[7] .................. A61K 39/00; A61K 45/00; A61K 31/70

(52) U.S. Cl. ................. 424/184.1; 424/283.1; 514/53; 514/54

(58) Field of Search .............. 514/53, 54; 424/184.1, 424/283.1

(56) References Cited

FOREIGN PATENT DOCUMENTS

EP  XP-000942421  of 1999

*Primary Examiner*—Elli Peselev
(74) *Attorney, Agent, or Firm*—Elliot Olstein; Alan J. Grant

(57) ABSTRACT

The present invention provides immunogenic compositions and methods for inducing enhanced immune responses using an antigen by use of an adjuvant comprising a member selected from a Caulobacter (in particular, *C. crescentus*) LPS or a fragment or derivative thereof.

7 Claims, 7 Drawing Sheets

ND4 Swiss Webster imm. with 20 ug pilus protein + PBS, MF59 or 25 ug Caulobacter LPS
9 wk boost  SC  SP 101 anti-Fim H his tag T3 responses

| | | | | | |
|---|---|---|---|---|---|
| PBS | 100 | 100 | 100 | 100 | 100 |
| PBS + Fim CH | 102400 | 102400 | 409600 | 819200 | 1638400 |
| MF 59 | 100 | 100 | 100 | 100 | 100 |
| MF 59 + Fim CH | 409600 | 409600 | 3276800 | 6553600 | 6553600 |
| R-LPS | 100 | 100 | 100 | 100 | 100 |
| R-LPS + Fim CH | 204800 | 204800 | 1638400 | 6553600 | 6533600 |
| S-LPS | 100 | 100 | 100 | 100 | 100 |
| S-LPS + Fim CH | 204800 | 204800 | 1638400 | 3276800 | 1638400 |
| P-Glyco | 100 | 100 | 100 | 100 | 100 |
| P-Glyco + Fim CH | 204800 | 204800 | 1638400 | 3276800 | 819200 |
| P-LPS | 100 | 100 | 100 | 100 | 100 |
| P-LPS + Fim CH | 102400 | 204800 | 3276800 | 3276800 | 819200 |

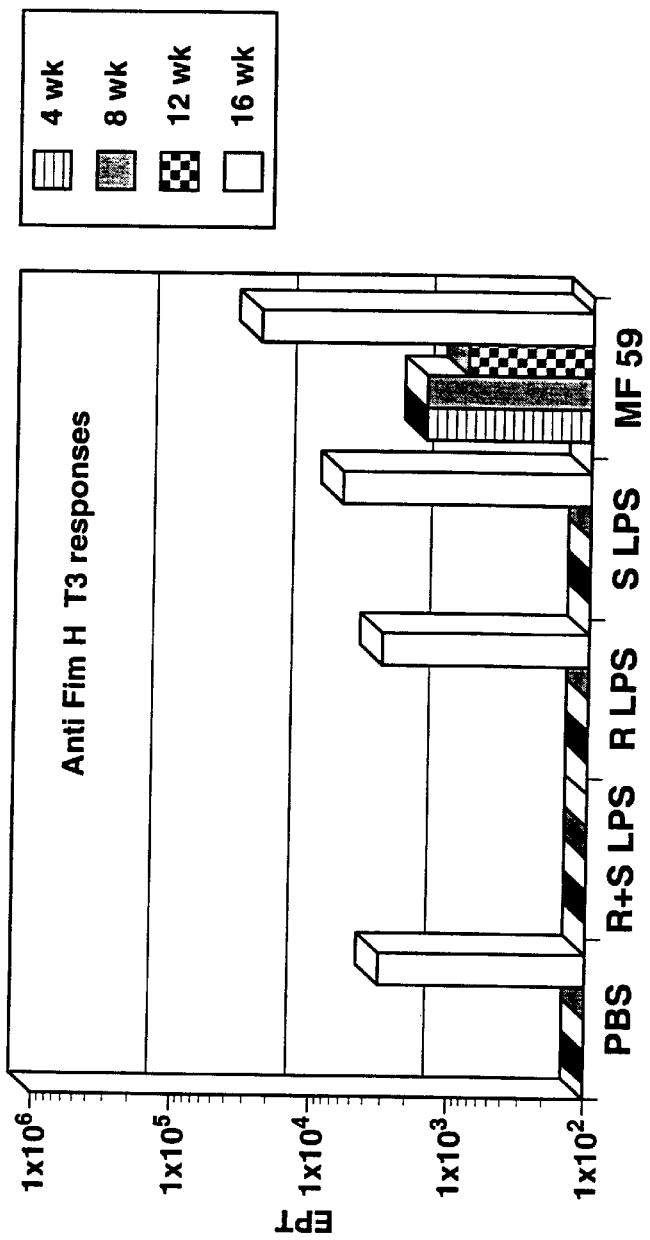

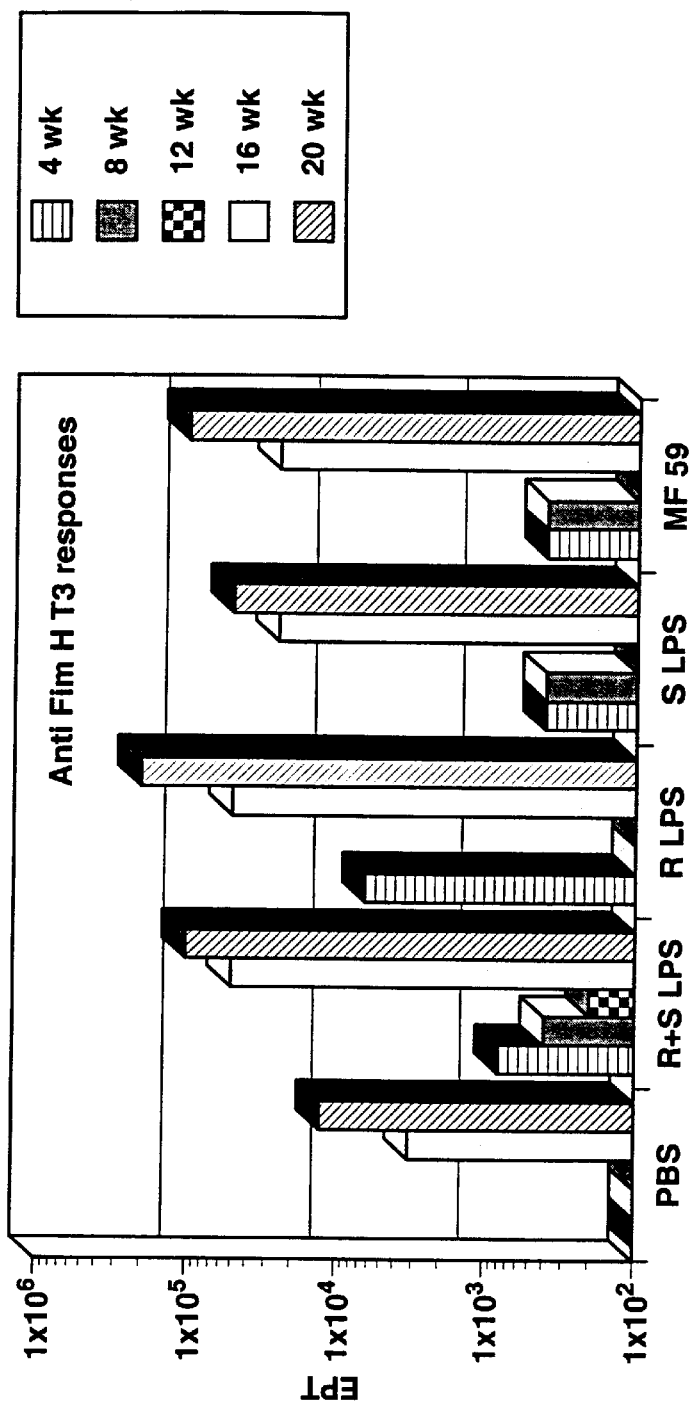

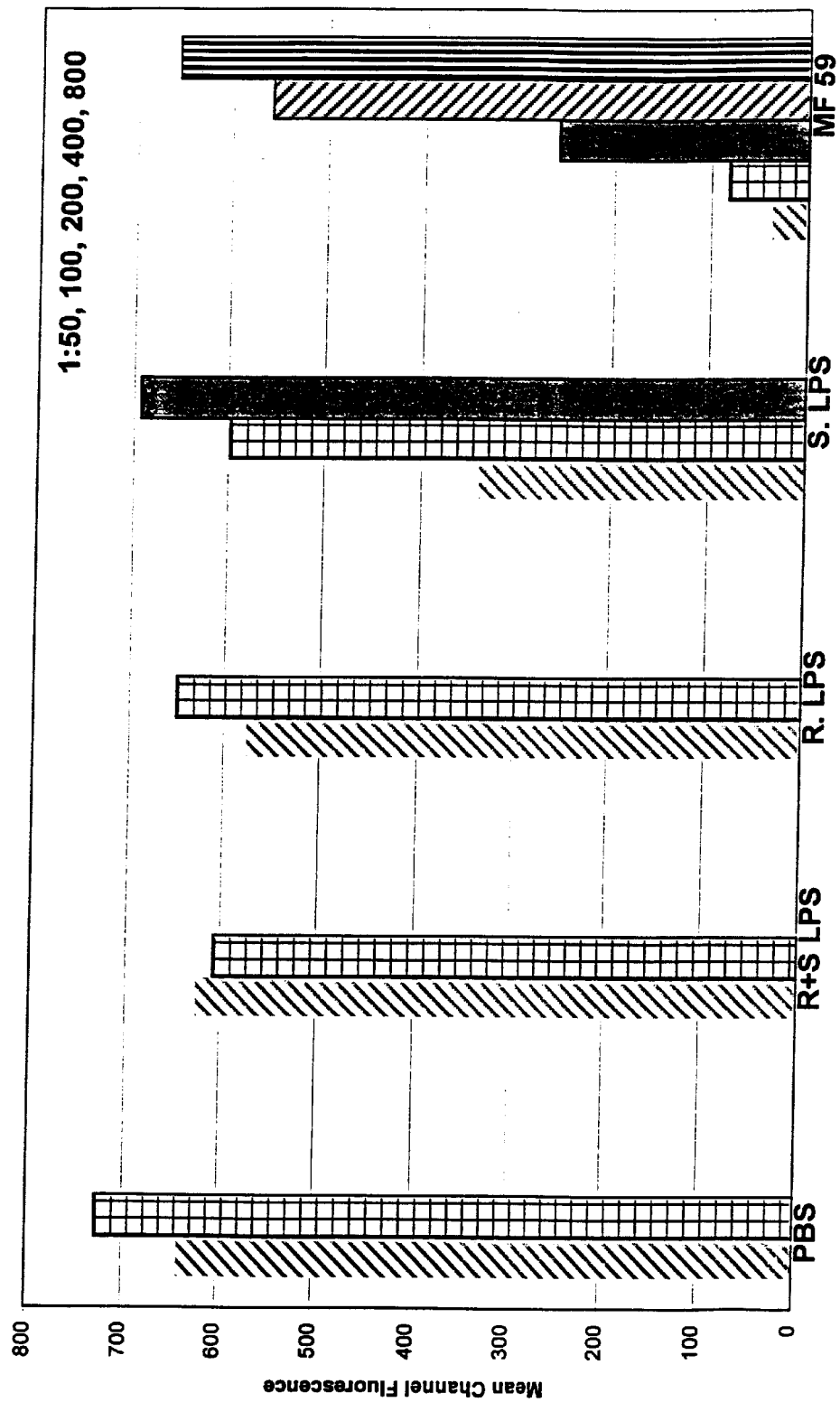

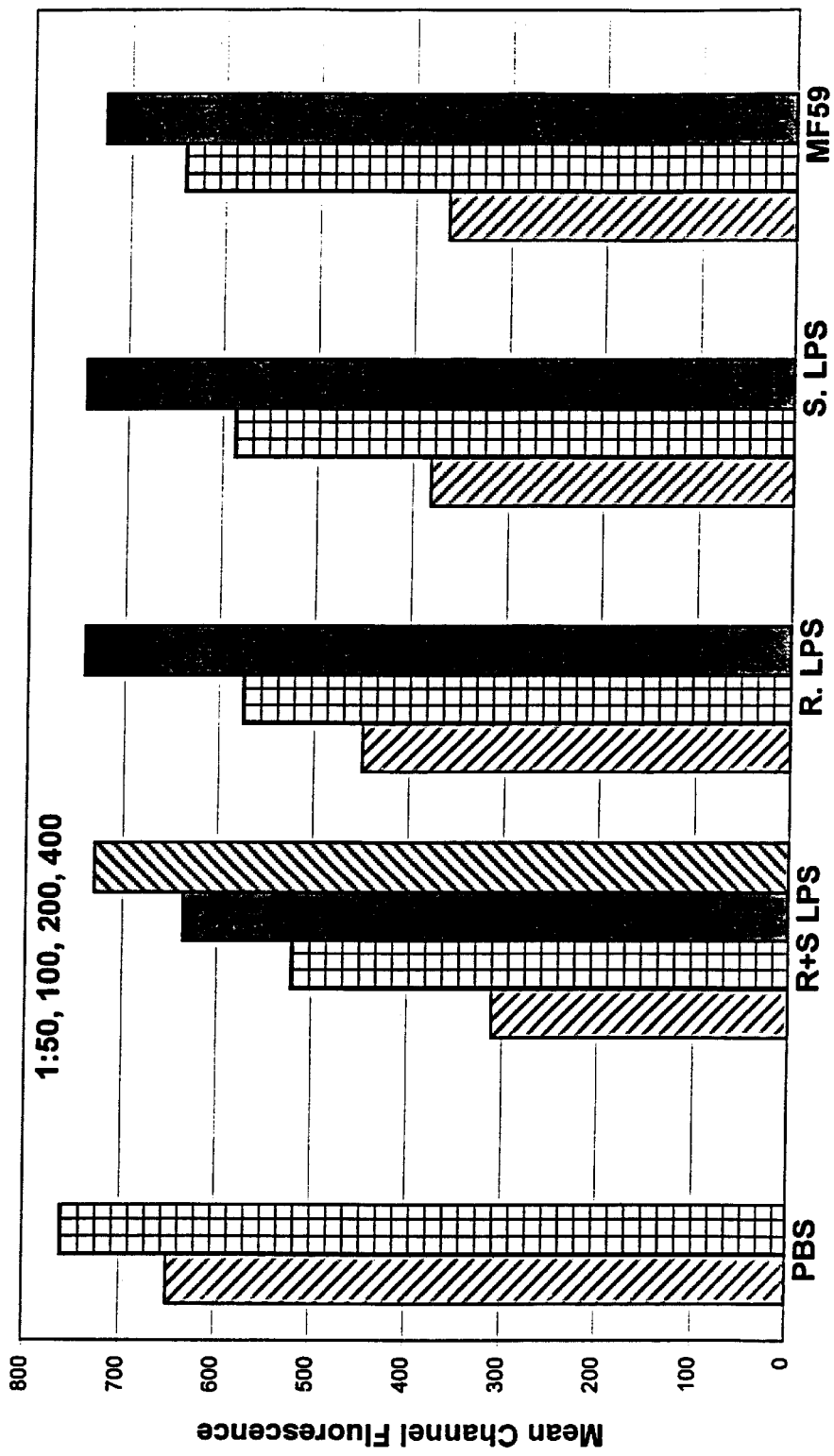

CAULOBACTER LPS IMMUNOADJUVANTS

This application claims the benefit of U.S. Provisional Application No. 60/121,120, filed Feb. 22, 1999, the disclosure of which is hereby incorporated by reference in its entirety.

FIELD OF THE INVENTION

This application relates to the field of lipopolysaccharides (LPS) that are useful as immunoadjuvants for vaccines and vaccines comprising such immunoadjuvants.

BACKGROUND OF THE INVENTION

A wide variety of antigens stimulate the production of antibodies in animals and confer protection against subsequent infection. However, some antigens stimulate only a mild or ineffective immune response while some are unable to stimulate an effective immune response.

The immunogenicity of a relatively weak antigen is often enhanced by the simultaneous administration of the antigen with an adjuvant, which is a substance that may or may not be immunogenic when administered alone, but will induce a state of mucosal and/or systemic immunity for an antigen when it is administered concurrently or proximate to the time that the antigen is administered. Unfortunately, many immunoadjuvants, such as Freund's Complete Adjuvant, are toxic and are therefore only useful for animal research purposes, not human vaccinations.

Preferred adjuvants are substances that are not immunogenic or very toxic when administered alone, but potentiate and focus the immune response to a vaccine. Adjuvants often contain immunomodulators that induce the production of cytokine cascades and result in an augmented immune response. Examples of immunomodulators include certain water-soluble polymers, muramyl peptides, lipopolysaccharides (LPS) from gram-negative bacteria and derivatives, and cationic detergents.

The outer membrane of characterized gram-negative bacteria is composed of phospholipids, proteins, lipopolysaccharide (LPS), and if present, extracellular polysaccharide, all of which interact to form a permeability barrier towards the aqueous milieu. Of these components, it is the LPS or extracellular polysaccharide that first meets the extracellular environment and, if an LPS-layer is present must in some way accommodate its attachment.

LPS from gram-negative bacteria, also known as endotoxin, has been recognized as a potent immunomodulator. In fact, the adjuvant-active component of LPS endotoxins of gram negative bacteria has been identified as lipid A (See FIG. 1 of Chapter 21, entitled "Monophosphoryl Lipid A as an Adjuvant" by Ulrich and Myers, from the book *Vaccine Designs: The Subunit and Adjuvant Approach*, ed. By Powell and Newman, Plenum Press, New York (1995)). Unfortunately, lipid A is pyrogenic and elicits a number of undesired side effects (see, for example, the MiniReview by Raetz, in Journal of Bacteriology, pages 5745–5753 (September 1993), entitled "Bacterial Endotoxins: Extraordinary Lipids That Activate Eucaryotic Signal Transduction"). Efforts have been made to separate the adjuvant activity from toxicity. The work of Raetz as described above relates to the structure of *E. coli* lipid A and of a portion of lipid A, as well as their use as an adjuvant. The structure of the lipid A endotoxin varies depending upon the type of bacteria from which it is obtained.

In general, lipid A is a disaccharide of glucosamine with two phosphate groups (at the 1' and 4' positions of the disaccharide) and five or six fatty acid side chains. Under mildly acidic conditions, one phosphate group can be removed leaving 4'-monophosphoryl lipid A (MPL). This molecule retains adjuvant activity but is much less toxic than lipid A. MPL, when formulated appropriately, can be used in humans. MPL, which is derived from *Salmonella minnesota* bacteria is the basis of the commercial adjuvant known as the RIBI MPL adjuvant.

*Caulobacter crescentus*, a stalked, gram-negative bacteria, contains an atypical LPS molecule (see, Ravenscroft et al., Journal of Bacteriology, 7595–7605 (December 1992), article entitled, "Membrane Lipopolysaccharide of *Caulobacter crescentus*"). Therein, LPS from such bacteria is described as being of a rough type in that it did not contain heterogeneous O antigen attached to the core sugars. The lipid A equivalent region and core oligosaccharide region were found to be quite distinct from all other LPS molecules. More recent analysis has shown that Caulobacter possess both rough and smooth LPS, the smooth LPS being the rough LPS-equivalent with the addition of a homopolymer antigen of perosamine (with about 40 copies of this sugar). However, nothing is known about the immunomodulating properties of Caulobacter LPS.

Although LPS from gram negative bacteria or portions thereof have been used as immunoadjuvants, it cannot be predicted whether or not an LPS is suitable for use as an adjuvant in that the LPS must not only have adjuvant properties but must also not have a toxicity level that would render the LPS non-suitable for use as an adjuvant. In addition, there is a continued need for adjuvants that are less toxic. In this respect, there is a need, inter alia, to identify naturally occurring LPS molecule(s) with adjuvant properties but with an attenuated (or negative) toxicity profile.

BRIEF DESCRIPTION OF THE DRAWINGS

FIG. 4 shows the results of immunization of C3H/HeJ mice with FimCH as antigen, using 0.25 $\mu$g FimCH, and 50 $\mu$g of the adjuvant IM on day 0 followed by a 15 week boost. The greatest result was observed at week 16 for the MF59.

FIG. 5 shows adjuvanticity of the Caulobacter LPS in C3H/OuJ mice using FimCH (0.25 $\mu$g) with 50 $\mu$g of the adjuvant IM on day 0 with a 15 week boost. Higher effects were seen at 20 weeks with R (rough) LPS.

FIG. 6 shows the results of collection of 20 week sera (with boost at 16 weeks) for Caulobacter LPS versus the MF59 Adjuvants in C3H/HeJ mice.

FIG. 7 shows the results of collection of 20 week sera (with boost at 16 weeks) for Caulobacter LPS versus the MF59 Adjuvants in C3H/OuJ mice.

SUMMARY OF THE INVENTION

Figure 1:
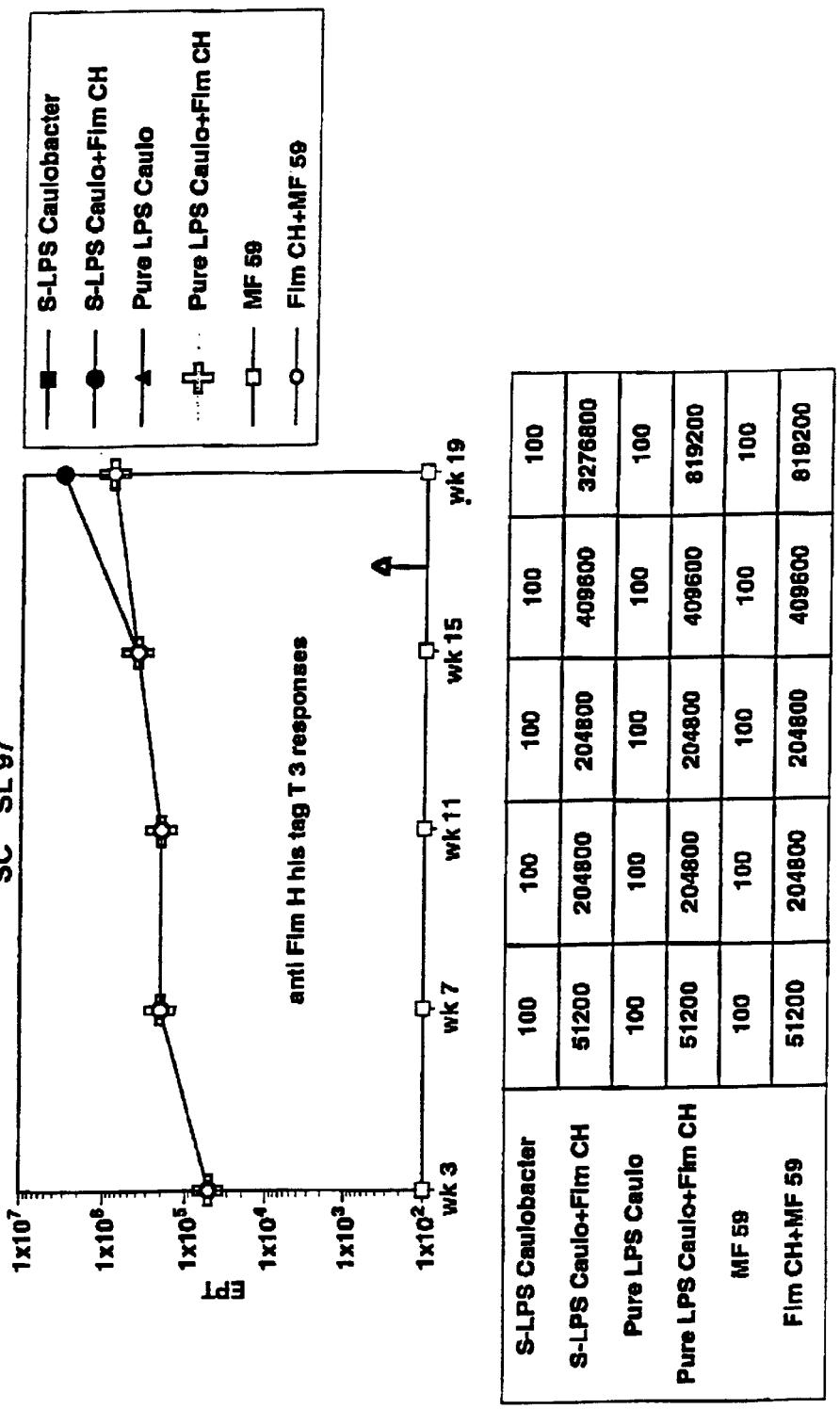
FIG. 1 shows the results of an immunization study on six groups (identified at the side of the table) of ND4 Swiss Webster mice (5 mice per group) with the values in the table plotted in the above graph. Pooled sera were used to show responses to the FimH antigen. The strongest response was to the S-LPS preparation. EPT=End Point Titer (to FimH).

The present invention relates to a novel adjuvant or immunization composition comprising a Caulobacter LPS or fragment thereof having adjuvant properties. For example, the fragment may be LPS lipid A, a LPS lipid A fragment, or a derivative thereof, having adjuvant properties. Preferably, such adjuvants are obtained from *Caulobacter crescentus*.

In a further aspect, the present invention provides a Caulobacter LPS or fragment thereof having adjuvant properties which is less toxic than other gram-negative LPS molecules. Preferably such adjuvant is LPS or lipid A, a lipid A fragment, or a derivative thereof, having adjuvant properties that are less toxic than other gram-negative LPS molecules and are derived from *C. crescentus*. As a representative example of a lipid A derivative, there may be mentioned the monophosphorylated derivative of the lipid A fragment of the LPS of *C. crescentus*. Such derivative may be prepared by monophosphorylating the lipid A fragment by procedures known in the art with respect to lipid A fragments from the LPS of other bacteria.

In another aspect, the present invention provides a method of inducing an immunogenic response in a host, in particular, a protective response when the adjuvant composition described in the above embodiments is administered orally, intramuscularly or parenterally concurrently with or proximately to the administering of an antigen. In one aspect, the adjuvant is mixed with the antigen prior to administration.

It is a further object of the invention to provide a vaccine for treating or preventing bacterial infections which utilizes the adjuvant according to the invention as set forth in the above objects of the invention and utilizes as an antigen a complex of a bacterial periplasmic chaperone protein with a bacterial adhesin protein. Preferably, the antigenic adhesin protein is a pilus adhesin protein. In one aspect, the antigenic periplasmic chaperone protein and pilus adhesin protein are from *E. coli;* for example, a member selected from the complexes PapD/PapG and FimC/FimH.

In a particular aspect, the invention relates to vaccines formulated with the adjuvant according to the invention and from an antigen which is a type 1 pilus-associated adhesin (or from a mannose-binding fragment thereof) or from antigens which are complexes of chaperone proteins and pilus-associated adhesins for the treatment and/or prophylaxis of diseases caused by pathogenic species of gram-negative bacteria, such as *Escherichia coli* (*E. coli*). For example, it relates to treatment and/or prophylaxis of urinary tract infections caused by *E. coli* with vaccines formulated with the adjuvant according to the invention and from an antigen which is selected from at least one of (1) a fragment of the pilus-associated adhesin FimH that retains mannose binding capability (alone or complexed with its chaperone FimC), (2) the pilus-associated adhesin PapG protein complexed with its periplasmic chaperone protein PapD or (3) the full-length pilus-associated adhesin FimH (alone or in a complex with its chaperone protein FimC). This invention also relates generally to the use of the adjuvant according to the invention in combination with heteropolymeric protein complexes to raise antibodies in non-human mammalian species useful, for example, as diagnostic reagents and vaccines.

In a further aspect of the present invention, Caulobacter adjuvants according to the invention are used in concert or combination with antigens to produce a vaccine which is useful as a therapeutic for treatment of a disease.

*Caulobacter crescentus* is a stalked, gram-negative bacteria and contains an atypical LPS molecule which has been generally described. LPS from such bacteria have been described as being of a rough type (R type LPS) in that it does not contain heterogeneous O antigen attached to the core sugars. The lipid A equivalent region and core oligosaccharide region are distinct from other LPS molecules. *Caulobacter crescentus* possesses both rough (R type) and smooth (S type) LPS, the smooth LPS being the rough LPS-equivalent with the addition of a homopolymer antigen of perosamine (with about 40 copies of this sugar). The LPS produced by such Caulobacter comprises an inner core region containing three 2-keto-3-deoxyoctulosonate (KDO) molecules, two α-L-glycero-D-mannoheptose and one α-D-glycero-D-mannoheptose; an outer core region of α-D-mannose, α-D-galactose, and α-D-glucose (possibly phosphorylated); and a lipid A portion contain 3-OH-dodecanoic acid attached to a backbone having an undetermined structure.

However, prior to the present invention, nothing was known about the immunomodulating properties of Caulobacter LPS.

*Caulobacter crescentus* strains are grown, and LPS isolated, and purified as described by Ravenscroft et al., Journal of Bacteriology, 7595–7605 (December 1992), which is incorporated herein by reference.

Additionally, Caulobacter strains can be grown in known media such as peptone-yeast extract under standard culturing conditions and LPS isolated by known methods. Such methods may include nuclease digestion of the disrupted cells followed by incubation with solutions that cause the Caulobacter cell membranes to dissociate more completely. Samples of LPS can be purified by well-known procedures followed by, or including, electrophoresis and/or chromatography.

For example, the rough LPS of Caulobacter can be extracted by the modified Galanos method (described in Quereshi et al, J. Biol. Chem. 258:12947–12951 (1983), incorporated herein by reference) and examined by Thin Layer Chromatography (TLC) and/or SDS-PAGE to determine purity. The smooth LPS of Caulobacter can be purified by NaCl/EDTA extraction and elution from an SDS-PAGE prep gel, followed by extensive washing on an Amicon 30,000 MW cutoff filter against distilled water to remove impurities. MALDI-TOF analysis can be utilized to show that the Caulobacter LPS has a molecular weight of about 10,400 daltons. Gas chromatography of the hydrolyzed LPS contains a homopolymer of a dideoxyaminohexose, tentatively identified as perosamine.

LPS can be cleaved into Lipid A and polysaccharide using 0.1 N HCl at 100° C. for 30 minutes, followed by extraction with 2.5 volumes of chloroform/methanol (2:1) per volume of aqueous LPS. The lipid A partitions to the chloroform/methanol (or lower) phase, which is then evaporated to dryness in a stream of dry nitrogen gas. The composition of the samples can be determined by standard analytical procedures, such as gas chromatography and the like. Dephosphorylation of LPS samples can be performed by utilizing HF and then removing the HF. Lipid analysis and NMR structural studies can be conducted by known methods.

Thus, the present invention provides a LPS from Caulobacter, or a fragment or derivative thereof, which enhances an immune response to an antigen, as well as adjuvant or vaccine compositions comprising them. The LPS may be in rough or smooth form. The adjuvant may be comprised of mixtures of the rough and smooth form, or either form alone, or may be comprised of a lipid A fragment or derivative of such fragment, alone or in combination with LPS.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to a polynucleotides, such terms refer to the products produced by treatment of said polynucleotides with any of the common endonucleases.

The present invention further provides a method of inducing an immunogenic response in a host (a human or a non-human animal), in particular, a protective response when the adjuvant composition according to the present invention is administered orally, intramuscularly or parenterally concurrently with or proximately to the administering of an antigen. In one aspect, the adjuvant is mixed with the antigen prior to administration. Alternatively, the adjuvant composition is administered proximately to the time of administering the antigen, but is not mixed with the antigen prior to administration.

The antigen useful in practicing the present invention can be derived from a cell, bacteria, or virus particle, or portion thereof. As defined herein, antigen may be a protein, peptide, polysaccharide, glycoprotein, glycolipid, nucleic acid, or combination thereof, which elicits an immunogenic response in an animal, for example, a mammal, bird, or fish. As defined herein, the immunogenic response can be humoral or cell mediated. In the event the material to which the immunogenic response is to be directed is poorly antigenic, it may be conjugated to a carrier such as albumin or to a hapten, using standard covalent binding techniques, for example, with one of the several commercially available reagent kits.

Examples of antigens include viral proteins such as influenza proteins and hepatitis B proteins; and bacterial proteins and lipopolysaccharides such as gram-negative bacterial cell wall and surface proteins.

The adjuvant can also be covalently conjugated with the antigen in accordance with methods well-known to those skilled in the art, usually by covalent linkage between an amino or carboxyl group on the antigen and one or more side groups on the adjuvant. Although in the preferred embodiment the adjuvant and antigen of the vaccine composition are administered simultaneously, in an alternative embodiment, the adjuvant and antigen are administered separately to the same site or to nearby sites. The adjuvant serves to attract cells of the immune system to the site where they then act upon the antigen.

The immunogenic composition can be administered as a vaccine by any method known to those skilled in the art that elicits an immune response, including parenterally, orally, or by transmembrane or transmucosal administration. Preferably, the vaccine is administered parenterally (intravenously, intramuscularly, subcutaneously, intraperitoneally, etc.), and preferably subcutaneously. Non-limiting examples of routes of delivery to mucosal surfaces are intranasal (or generally, the nasal associated lymphoid tissue), respiratory, vaginal, and rectal. In the vaccine, the adjuvant is added in an amount effective to increase or potentiate the immune response to an antigen. The immune response can be a protective immune response or an immune response effective for treating a disease or condition.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON'S PHARMACEUTICAL SCIENCES (Mack Pub. Co., New Jersey current edition).

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

EXAMPLE 1

LPS was isolated from *C. crescentus* by a variation of the method disclosed in Walker et al, J. Bacteriol. 176:6312–6323 (1994). The LPS is purified by NaCl/EDTA extraction (as disclosed therein), including the recited subsequent steps of treatment with SDS, proteinase K, and extensive dialysis against distilled water and lyophilization. The dried LPS is then extracted 3 times with chloroform (3:1) and suspended in water (and designated "SLPS"). A portion is further purified by making the SLPS aqueous solution to 0.1 M EDTA followed by 2 extractions with 2.5 volumes of chloroform/methanol (2:1) per volume of aqueous LPS, retaining the aqueous phase each time. This preparation is designated "P-LPS."

Six groups of ND4 Swiss Webster mice were used in this first study (5 mice per group). Group 1 received S-LPS adjuvant alone (100 μg dose), Group 2 received S-LPS (100 μg)+FimCH (20 μg), Group 3 received P-LPS (100 μg dose), Group 4 received P-LPS+FimCH (20 μg), Group 5 received MF59 as a positive control (1:1 volume/volume with 50 μl of PBS) and Group 6 received MF59+FimCH (1:1 volume/volume with 50 μl of a 20 μg dose of FimCH). Mice were immunized on Day 0 and boosted at 17 weeks. Bleeds were obtained on day 0 (prior to immunization) and at weeks 3, 7, 11, 15 and 19 after immunization. Pooled sera samples from each group were evaluated for immune responses to the FimH antigen (using a FimH truncate "T3" as a capture antigen in ELISA assays). The results of this immunization Study #1 are shown in FIG. 1, as reciprocal endpoint titers (EPT) to FimH. The strongest response in this study was seen to the S-LPS preparation, prepared by the NaCl/EDTA extraction protocol. The response to the re-extracted P-LPS preparation was comparable to the MF59 adjuvant (positive control).

Figure 2:
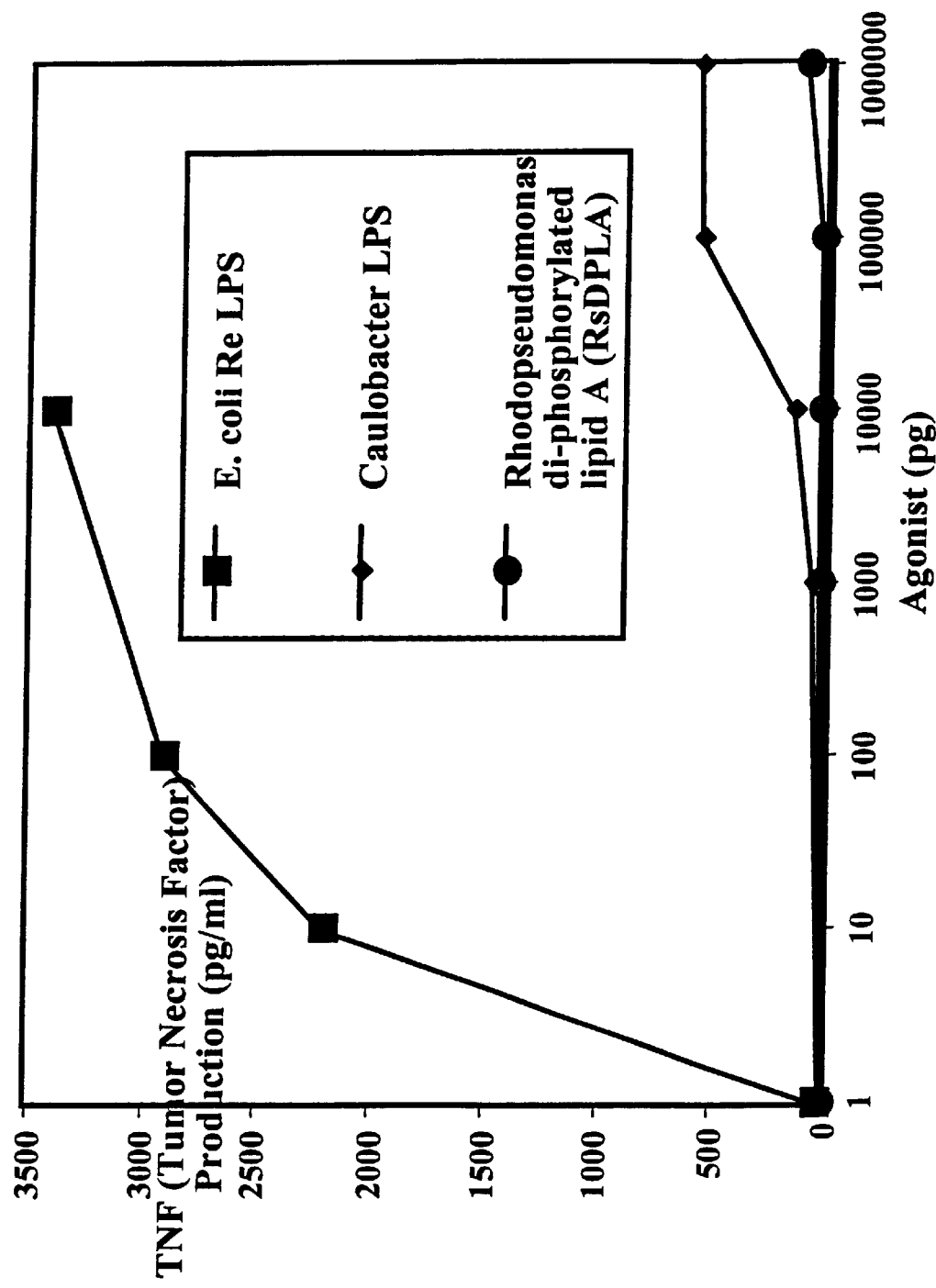
FIG. 2 shows toxicity data for the induction of TNF (tumor necrosis factor) using a standard in vitro assay. TNF-$\alpha$ production was monitored by ELISA.

Prior to testing the S-LPS and P-LPS in mice, each of these preparations was evaluated for toxicity utilizing a standard in vitro assay for cytotoxicity. RAW 264.7 murine macrophages (ATCC, Rockville, Md.) were grown in Dul-Becco's modified Eagle Medium, supplemented with 10% fetal calf serum, and 1% L-glutamine, with 1% penicillin/streptomycin. After growth to confluence, RAW macrophages were stimulated with varying concentrations of Caulobacter LPS (or *E. coli* LPS) overnight (for 18 hours), and supernatants were tested by Enzyme Linked Immunosorbant Assays (ELISA) for TNF-α production. The results are shown in FIG. 2.

The ability of antibodies to the FimH adhesin to prevent bacterial binding to mannose (the receptor for FimH on uroepithelial cells) was investigated in vitro, as a measure of the functional antibody to FimH elicited by each of the LPS adjuvant preparations. The assay was done as follows: Immulon-4, 96-well ELISA plates were coated with 2.5 μg/ml (100 μl/well) of trimannose. After blocking the plates with PBS-1% BSA, type 1-piliated *E. coli* were added to each well @ $8\times10^7$ CFU/ml) in the presence of anti-FimH antibodies from each of the groups of mice cited above or negative control antisera (adjuvant alone) or no antibody, and allowed to incubate and bind to the plates for 1 hour at 37° C. Unbound bacteria were washed away and *E. coli* which remained attached to the trimannose was detected with a 1:400 dilution of rabbit anti-*E. coli*-HRP antiserum, followed by the addition of TMB substrate. The results for the 19 week bleed (post boost) are shown in Table 1. Data are presented as percent inhibition binding to trimannose as compared to positive control (no antibody).

TABLE 1

In vitro Binding of Type 1 - Piliated *E. coli* to Tri-Mannose (Receptor for FimH ligand) and Inhibition by Anti-FimH Antisera Raised With Caulobacter LPS Adjuvants (SL97) or MF59

| Adjuvant/Antigen | % Inhibition Binding to Trimannose (19 wk bleed; 1:50 dilution) |
|---|---|
| S-LPS (no FimCH) | 0 |
| S-LPS + FimCH | 52 |
| P-LPS (no FimCH) | 0 |
| P-LPS + FimCH | 64 |
| MF59 (no FimCH) | 0 |
| MF59 + FimCH | 66 |
| Naive Serum | 0 |

EXAMPLE 2

*Caulobacter crescentus* cells are subjected to the modified Galanos method (Quereshi et al, J. Biol. Chem., 258:12947–12951 (1983)) to recover RLPS. SLPS is purified from *C. crescentus* cells by the NaCl/EDTA extraction method disclosed in Walker et al, J. Bacteriol. 176:6312–6323 (1994), including the subsequent steps of treatment with SDS, proteinase K, and extensive dialysis against distilled water. For this experiment the SLPS was further purified by preparative SDS-PAGE, followed by electro-elution of the SLPS band from the gel and extensive washing of the eluted SLPS on an Amicon 30,000 MW cutoff filter with distilled water to remove impurities. An impurity recovered from the PLPS of Example 1 as a precipitate resulting from treatment of PLPS with 7.5% MgCl$_2$ in cold 95% ethanol was tentatively labeled "glycolipids" but was found to contain some SLPS.

LPS of *C. crescentus,* isolated as in Example 1, is subjected to the Galanos extraction method (Eur. J. Biochem. 9:245–49) to recover rough LPS (RLPS). The remaining portion is subjected to NaCl/EDTA extraction, as in Example 1, followed by electroelution from an SDS-Page prep gel to recover smooth LPS (SLPS). The impurity recovered from the gel is labeled provisionally as "glycolipids," but also contains some smooth LPS.

The PLPS is the material from Example 1.

Protocol for Immunizations:
  Mouse strain: ND4 Swiss Webster
  Mice per group: 5
  Number of groups: 12
  Immunization schedule: Immunize on day 0, bleed every 3 weeks to determine end point titers and functional inhibitory titers. Boosted at 9 weeks.
  Route of Immunization: Subcutaneous
  Dose: 25 μg of each LPS adjuvant, 20 μg FimCH, usual amount of MF59 (1° and Boost)

| Group # | Adjuvant | Antigen |
|---|---|---|
| 1 | PBS | None |
| 2 | PBS | FimCH |
| 3 | MF59 | None |
| 4 | MF59 | FimCH |
| 5 | Sample a RLPS | None |
| 6 | Sample a RLPS | FimCH |
| 7 | Sample b SLPS | None |
| 8 | Sample b SLPS | FimCH |
| 9 | Sample c purified glycolipids | None |
| 10 | Sample c purified glycolipids | FimCH |
| 11 | Sample d P-SLPS | None |
| 12 | Sample d P-SLPS | FimCH |

Results

Figure 3:
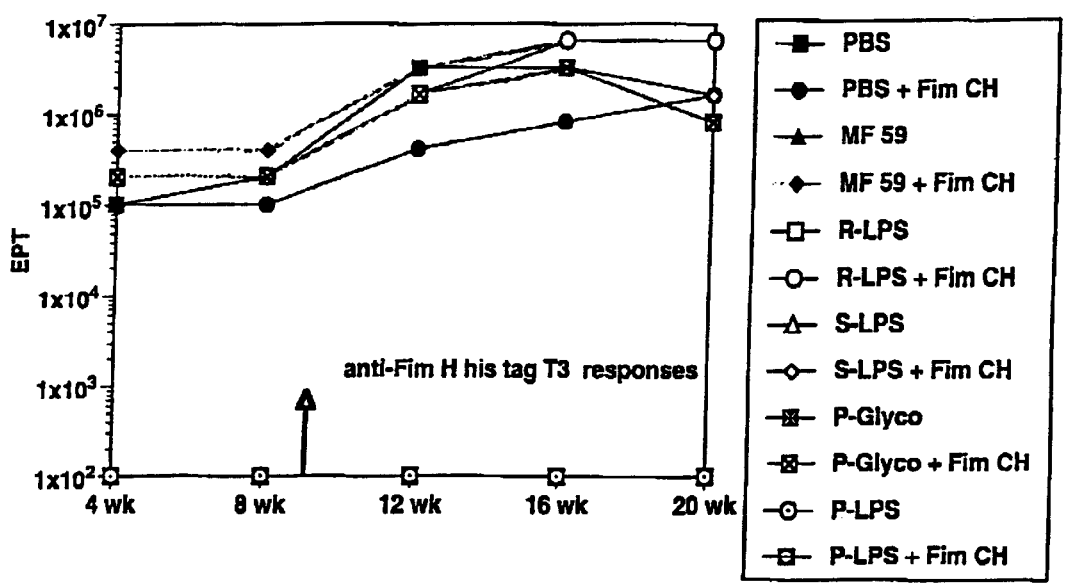
FIG. 3 shows the results of immunizations carried out according to the protocol set forth in Example 2. Strong adjuvant effects were seen with all of the purified fractions.

Strong adjuvant effects were seen with all purified fractions (R-LPS, S-LPS and "glycolipid fraction") [see FIG. 3]. Note that some rough LPS is present within both the S-LPS and glycolipid.

For these studies, 20 μg of FimCH as a fixed dose was used as the test antigen. However, this is not necessarily the optimum dose. In addition, the results of FIGS. 1–3 merely show the potential adjuvanticity properties of smooth, rough, and smooth+rough Caulobacter LPS preparations. Further, these studies were performed in C3H/HeJ mice (LPS non-responders) and C3H/OuJ mice (LPS responders) as well as the outbred ND4 Swiss Webster strain. For FimCH as test antigen (in phosphate buffered saline (PBS) alone with no adjuvant), additional studies have shown that FimCH induces endpoint titers (EPT) to the FimH protein (using a T3 ELISA assay) comparable to titers induced with other adjuvants (such as MF59) down to a FimCH dose of between about 0.25 μg to about 1.0 μg. Additional tests of the Caulobacter LPS adjuvants (R, S and R+S) with both 0.25 μg and 1.0 μg of FimCH in both C3H/HeJ and C3H/OuJ mouse strains were performed. The results for 0.25 μg are shown in FIGS. 4 and 5 for the C3H/HeJ and C3H/OuJ mouse strains, respectively.

In vitro binding to human tissues, purified receptors or receptor homologs is often used to elucidate the roles in virulence of many different bacterial adhesins, including pilus-associated adhesins. In a similar way, assaying for the ability of such antibodies to block attachment of bacteria to cells or specific receptors can assess the functionality of antibodies to adhesins.

The ability of the anti-FimH adhesin antibodies to block bacterial binding to bladder epithelial cells was investigated in vitro using a flow cytometric method originally developed for evaluating Rickettsia-cell attachment (see: Li and Walker, *Infectious Immunity*, 60:2030–2035 (1992)). This assay was adapted as follows: Type-1 piliated cystitis isolate NU14 (Hultgren et al, *Infectious Immunity*, 54:613–620 (1986)) were directly labeled with fluorescein isothiocyanate. (FITC) and incubated with $0.5 \times 10^6$ J82 bladdercells, at a ratio of 250 bacteria/cell, in the presence of pre-immune or hyper-immune serum (murine or primate antisera) and allowed to mix with the bacteria for 30 minutes at 37° C. After multiple washes, samples were assayed by flow cytometry in a FACStar PLUS (Becton Dickinson) according to previously published methods (Langermann et al, *Science*, 276: 607–611 (1997)). Mean channel fluorescence was used as an indicator of FITC-labeled bacteria bound to J82 bladder cells. The percent inhibition was determined relative to pre-immune samples taken from each animal. All serum samples were two-fold diluted (ranging from 1:50 to 1:800) in PBS prior to analysis.

The results for antisera from both C3H/HeJ and C3H/OuJ mouse strains immunized with FimCH+Caulobacter LPS preparations are shown in FIGS. 6 and 7.

The results clearly show that Caulobacter LPS has useful adjuvant properties in terms both of inducing endpoint titers and functional inhibitory titers to FimH comparable to other adjuvants. The observed responses seem to correlate with LPS responsiveness in-the mice (the C3H/OuJ mouse strain has higher endpoint titers and better functional activity than the C3H/HeJ mouse strain when receiving specifically the LPS adjuvants).

What is claimed is:

1. A composition for inducing an immunogenic response in an animal comprising an antigen and at least one member selected from the group consisting of Caulobacter LPS and a fragment of Caulobacter LPS wherein said member has adjuvant properties.

2. The composition of claim 1 wherein the Caulobacter is *Caulobacter crescentus*.

3. The composition of claim 1 wherein said member is a lipid A fragment of the LPS of *Caulobacter crescentus*.

4. The composition of claim 1 wherein the LPS is rough *Caulobacter crescentus*.

5. The composition of claim 1 wherein the LPS is smooth *Caulobacter crescentus*.

6. The composition of claim 1 wherein the member is Caulobacter LPS.

7. A method of inducing an enhanced immune response to an antigen comprising administering to an animal an antigen and an adjuvant, said adjuvant comprising at least one member selected from the group consisting of Caulobacter LPS and a fragment of Caulobacter LPS wherein said member has adjuvant properties.

* * * * *